(12) United States Patent
Finci et al.

(10) Patent No.: US 10,751,088 B2
(45) Date of Patent: Aug. 25, 2020

(54) GYNAECOLOGICAL MODULE AND APPARATUS

(71) Applicant: Aspivix SA, Lausanne (CH)

(72) Inventors: David Finci, Meyrin-Village (CH); Julien Finci, Meyrin-Village (CH); Mathieu Horras, Basel (CH)

(73) Assignee: ASPIVIX SA, Lausanne (CH)

( * ) Notice: Subject to any disclaimer, the term of this patent is extended or adjusted under 35 U.S.C. 154(b) by 43 days.

(21) Appl. No.: 15/533,894

(22) PCT Filed: Dec. 7, 2015

(86) PCT No.: PCT/IB2015/059415
§ 371 (c)(1),
(2) Date: Jun. 7, 2017

(87) PCT Pub. No.: WO2016/092458
PCT Pub. Date: Jun. 16, 2016

(65) Prior Publication Data
US 2017/0325843 A1    Nov. 16, 2017

(30) Foreign Application Priority Data
Dec. 8, 2014    (CH) ..................................... 1892/14

(51) Int. Cl.
*A61B 17/42*    (2006.01)
*A61B 1/303*    (2006.01)
(Continued)

(52) U.S. Cl.
CPC .............. *A61B 17/42* (2013.01); *A61B 1/303* (2013.01); *A61B 17/4241* (2013.01); *A61F 6/18* (2013.01);
(Continued)

(58) Field of Classification Search
CPC ..... A61B 1/303; A61B 10/0291; A61B 17/42; A61B 17/442; A61B 17/4241;
(Continued)

(56) References Cited

U.S. PATENT DOCUMENTS

| | | |
|---|---|---|
| 2,082,782 A | 6/1937 | Allen |
| 3,585,984 A | 6/1971 | Buchanan |

(Continued)

FOREIGN PATENT DOCUMENTS

| | | |
|---|---|---|
| EP | 0 088 714 | 9/1983 |
| EP | 2 226 016 | 9/2010 |

(Continued)

OTHER PUBLICATIONS

International Search Report and Written Opinion, issued in PCT/IB2015/059415, dated Feb. 19, 2016.

*Primary Examiner* — Katherine H Schwiker
(74) *Attorney, Agent, or Firm* — Medler Ferro Woodhouse & Mills PLLC

(57) ABSTRACT

A gynecological suction module (1) comprising a hollow rod (20) and a suction chamber (10) connected to the hollow rod by a hole (H) for fluid connection, the aforesaid suction chamber being configured to engage the surface of the vaginal portion of the cervix, the aforesaid suction chamber (10) being delimited by a concave wall W defined by an edge (P) having a C shape and comprising an external portion (P1), an internal portion (P2) and two end portions (P3, P3'), wherein said internal edge P2 is out of the plane defined by said external portion P1.

25 Claims, 5 Drawing Sheets

(51) Int. Cl.
*A61F 6/18* (2006.01)
*A61B 17/00* (2006.01)
*A61B 17/30* (2006.01)
*A61B 10/02* (2006.01)

(52) U.S. Cl.
CPC . *A61B 10/0291* (2013.01); *A61B 2017/00561* (2013.01); *A61B 2017/00907* (2013.01); *A61B 2017/306* (2013.01); *A61B 2017/308* (2013.01); *A61B 2017/4225* (2013.01); *A61B 2217/005* (2013.01)

(58) Field of Classification Search
CPC .... A61B 2017/4216; A61B 2017/4225; A61B 2017/445; A61B 2017/447; A61B 2017/306; A61B 2017/308; A61B 2217/005; A61B 2017/00561; A61B 2017/00566; A61F 6/18; A61F 6/16; A61F 6/14; A61F 6/142; A61F 6/144; A61F 6/146; A61F 6/148; A61F 2/08; A61F 2/12

USPC .......................................... 606/119, 121–124
See application file for complete search history.

(56) References Cited

U.S. PATENT DOCUMENTS

| | | | |
|---|---|---|---|
| 5,713,909 A | 2/1998 | Lindsay | |
| 5,772,630 A | 6/1998 | Ljungquist | |
| 6,013,027 A | 1/2000 | Khan et al. | |
| 6,059,795 A * | 5/2000 | Wallace | A61B 17/442 606/122 |
| 6,156,006 A | 12/2000 | Brosens et al. | |
| 2012/0283595 A1 | 11/2012 | Curtis et al. | |
| 2013/0291872 A1 | 11/2013 | Cappiello et al. | |

FOREIGN PATENT DOCUMENTS

| | | |
|---|---|---|
| WO | 00/32123 | 6/2000 |
| WO | 03/009766 | 2/2003 |
| WO | 2004/004583 | 1/2004 |

* cited by examiner

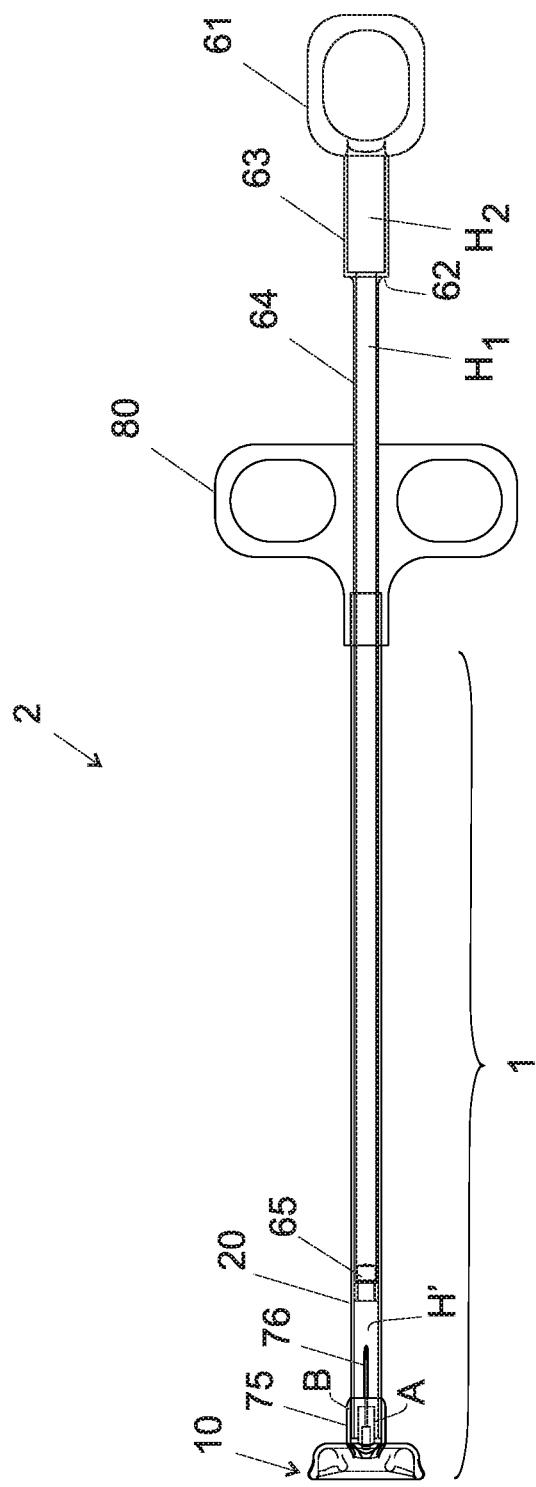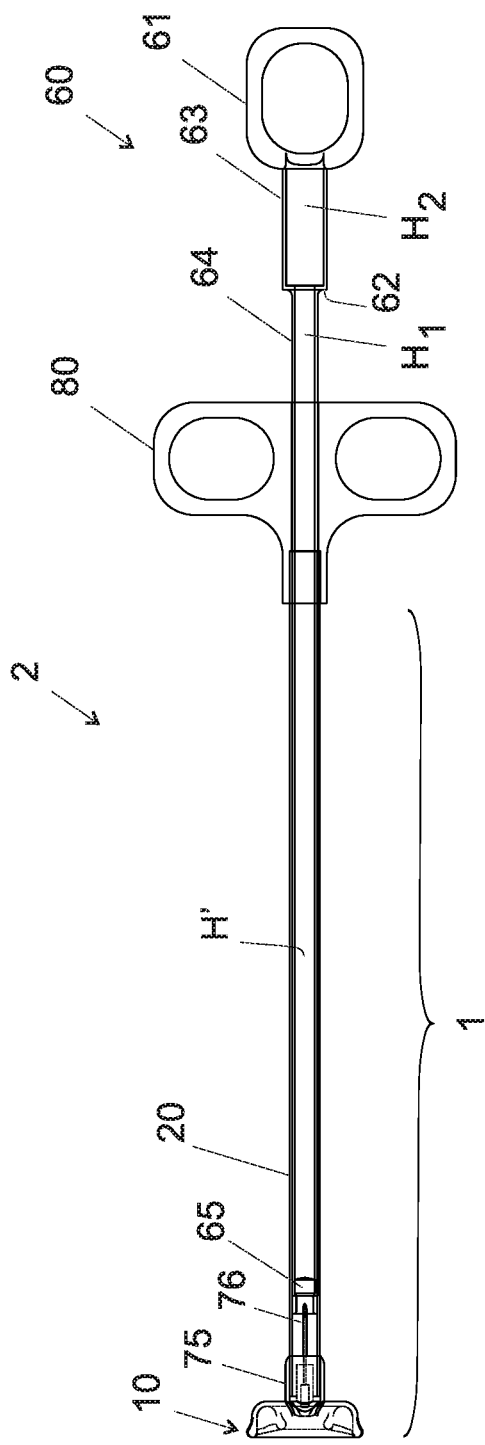

GYNAECOLOGICAL MODULE AND APPARATUS

FIELD OF THE INVENTION

The present invention concerns medical devices and methods used during multiple gynaecological procedures. More specifically, the present disclosure relates to methods and apparatus used to grasp and/or manipulate the cervix.

DESCRIPTION OF RELATED ART

Grasping cervix is essential in many very common gynaecological procedures, some listed below: IUCD (intra uterine contraception device) insertion and removal, uterine tissue swab (endometrial) for diagnostic purpose, cervix dilatation for uterus cavity curettage, cervix dilatation for hysteroscopy (camera in uterus), measuring uterine cavity size during surgery, hysterosalpingography (imaging procedure of the uterine cavity and fallopian tubes for fertility check-up).

To execute the procedures, the tenaculum also called Claw forceps or Pozzi with their dozen of variants have been used for over a century. This instrument which features stainless steel jaws ending in sharp inward-pointing hooks for cervix grasping. To achieve its grasping effectiveness, tenaculum is obviously painful, traumatic, triggering often bleeding and sometimes iatrogenic lesions of the cervix. Pozzi forceps, for the most performing of them, are non-disposable instruments, requiring sterilization between two procedures and of course a sterilization infrastructure. Moreover, no matter how the sterilization process is, non-disposable instruments are associated with a risk of contamination in case of inappropriate sterilization. Finally Pozzi forceps is in general a stainless steel instrument, the cold contact of which generates patient discomfort. Some solutions have offered plastic disposable tenaculum, being supposedly non-traumatic. While their non-traumatic aspect was unproven, the grasping effectiveness is seen as insufficient.

Despite of these clear drawbacks, due to lack of alternative, tenaculum is widely used in gynaecology and obstetrics to grip and pull the cervix.

Documents WO2004/004583, U.S. Pat. No. 2,082,782, US2013/291872, disclose instrument used for surgical operations to hold uterine parts. EP0088714 discloses a catheter for injecting a fluid into the uterus. EP2226016 discloses a sampling device consisting of an elongated tube.

US20120283595 proposes a solution where the cervix is grasped using uniformly distributed negative pressure and without the use or aid of teeth or prongs that may pierce, and possibly tear, tissue during use. However this solution uses a closed suction part with a form that renders the central tunnel too narrow, and does not allow all instruments to enter or exit preventing the correct execution of some gynaecological procedures. In addition, the cervix dilation is limited by the central tunnel diameter, which is fixed.

A problem encountered comes from the natural anatomy of females; the cervix is at an angle relative to the vaginal canal. Practitioners use a speculum to open the vagina and view the cervix before inserting the tenaculum. After insertion into the vagina, it allows grasping the external part of the cervix. Practitioners then pull the tenaculum jaws in the axis of the vagina. By exerting traction, practitioners correct the anatomical physiological flexion angle between the axis of the cervix and the body axis (uterus) necessary to access the uterine cavity through the cervical canal during surgery. However the practitioner does this correction manually.

GB2485967 proposes an obstetric vacuum extractor comprising a cylinder; a cup communicating with the cylinder; and a piston movable within the cylinder to evacuate the cup; wherein the piston is movable within the cylinder by a handle connected to the piston by an extensible bias element permitting relative movement of the handle with respect to the piston.

Another problem encountered is the visibility through the vagina during the execution of the procedure.

An aim of this invention is to propose a suction module without the drawbacks of the prior art systems.

BRIEF SUMMARY OF THE INVENTION

According to the invention, these aims are achieved by means of:

A gynaecological suction module, which comprises a hollow rod and a suction chamber, connected to the hollow rod by a hole for fluid connection. The suction chamber is configured to engage the surface of the vaginal portion of the cervix and is delimited by a concave wall W with an edge having a C shape.

The edge forms a closed loop, which comprises an internal edge portion, an external edge portion and two end edge portions. The end edge portions connect the internal edge portion to the external edge portion.

The external edge portion, the internal edge portion and the end edge portions are curved. The curvature of the external edge portion and of the end edge portions are directed towards the inside of the closed loop of the edge while the curvature of the internal edge portion is directed towards the outside of the closed loop of the edge.

The external edge portion, the internal edge portion and the end edge portions are arcs of a circle.

The end edge portions are semi-circles.

The internal and external portions define two angular sectors having the same center.

The aforesaid angular sectors define an angle $\alpha$ comprised between 10 and 350 degrees preferably between 50 and 230 degrees, preferably between 100 and 180 degrees, preferably between 125 and 155. In a preferred embodiment the aforesaid angular sectors define an angle $\alpha$ of about 140 degrees.

According to preferred embodiments the external radius $R1$ can be 10 mm or 12.5 mm or 15 mm or 17.5 mm, the internal radius $R2$ can be 5 mm or 7.5 mm or 10 mm or 12.5 mm. The radii $R1$ and $R2$ are depending on anatomy—might require to be designed in different sizes for different patients—and on vacuum level which is targeted. According to preferred embodiments the difference of radii $d1$ given by $R1-R2$ of the two angular sectors is 5 mm. In other variants, the difference of radii $d1$ is comprised between 1 and 50 mm, preferably between 2 and 25 mm, or between 3 and 10 mm.

A peripheral lip portion is placed along the edge in radially outwardly direction.

The aforesaid lip has a width between 1 and 10 mm or between 1 and 6 mm or between 2 and 4 mm, preferably 2.5 mm.

Preferably, the lip has a semi-circular section with a radius between 0.5 and 5 mm or between 0.5 and 3 mm or between 1 and 2 mm.

The suction chamber has a depth L between 3 and 20 mm or between 4 and 15 mm or between 5 and 10 mm, preferably 8 mm.

The hole is placed through the wall at an equal distance from the aforesaid external edge portion and from the aforesaid internal edge portion.

The diameter of the aforesaid hole is comprised between 0.1 and 20 mm or between 0.5 and 10 mm or between 1 and 5 mm, preferably 3 mm.

The hollow rod is rigid to move/pull the suction module accurately and precisely.

The hollow rod has an axial portion connected to the suction chamber and an inclined or curved portion adjacent to the axial portion to ensure an optimal field of view for the practitioner.

The inclined or curved portion of the hollow rod measures between 1 and 50 mm or between 10 and 30 mm or between 15 and 25 mm, preferably 20 mm.

The inclined or curved portion of the hollow rod forms an angle β with respect to the axis X-X' of the aforesaid axial portion which is comprised between 0 and 90 degrees or between 5 and 70 degrees or between 10 and 50 degrees or between 15 and 30 degrees, preferably 20 degrees.

The aforesaid axial portion of the hollow rod measures a length between 10 and 300 mm or between 50 and 250 mm or between 80 and 200 mm or between 100 and 150 mm, preferably 130 mm.

The hollow rod is made with transparent material to enhance the visibility for the practitioner.

In an embodiment the gynaecological suction module also comprises a vacuum reserve source and a connector to seal the rod with the vacuum source.

The vacuum reserve source has a pressure less than 500 mbar or less than 350 mbar or between 100 and 250 mbar, is depending on the global volume comprising the suction chamber and the rod.

The connector and the hollow rod can be made of one part directly from molding or rapid 3D printing or assembled by welding, gluing, or mechanical attachment with or without O-rings, preferably with a removable connection.

According to another embodiment the gynaecological suction module also comprises an apparatus wherein the vacuum system is a vacuum reserve rod defining a sealed enclosure and comprising an elongated portion with a distal end closed by a pierceable element, said elongated portion being placed at least partially within said hollow rod, said apparatus further comprising a hollow needle arranged for piercing said pierceable element when said elongated portion is placed within said hollow rod whereby the suction chamber is in tight fluid communication with said reserve source.

The elongated portion comprises a stop means. This stop means is arranged so that the longitudinal position of the elongated portion in the hollow rod is limited. This is a visual and secure way to be sure that the apparatus is placed in the second position where the sealed enclosure of the vacuum reserve rod communicates with the suction chamber.

The elongated portion comprises two cylindrical first and second portions attached together and said vacuum reserve rod further comprises a loop portion at a proximal end.

The second cylindrical portion has an outer diameter which is smaller than the inner diameter of the hollow rod. Preferably, the first cylindrical portion has an outer diameter which is bigger than the inner diameter of the hollow rod. In that case, a shoulder is defined between the first cylindrical portion and the second cylindrical portion, with said shoulder serving as stop means.

The pierceable element is a closing plastic layer, a rubber, a septum or a plug.

The hollow needle is mounted at the center of a cylindrical connecting part, it is able to connect in a sealed manner the hole of the suction chamber to the hollow rod.

The first cylindrical portion comprises a passage H2 preferably larger than the passage H1 of the second cylindrical portion.

The vacuum reserve rod has a negative pressure less than 350 mbar or less than 250 mbar or between 10 and 150 mbar.

The cylindrical first portion has a length between 1 mm and 100 mm or between 10 mm and 60 mm or between 20 mm and 50 mm, preferably 35 mm.

The suction chamber is engaged in a vaginal portion of a cervix, and creates a crescent suction chamber against a surface of the vaginal portion of the cervix.

BRIEF DESCRIPTION OF THE DRAWINGS

The invention will be better understood with the aid of the description of an embodiment given by way of example and illustrated by the figures, in which:

FIG. 8a shows a view of the whole apparatus in a first position in a second embodiment FIG. 8b shows a view of the whole apparatus in a second position in said second embodiment

DETAILED DESCRIPTION OF POSSIBLE EMBODIMENTS OF THE INVENTION

FIGS. 1 to 7 now described are in relation to a first embodiment of the invention.

Figure 1:
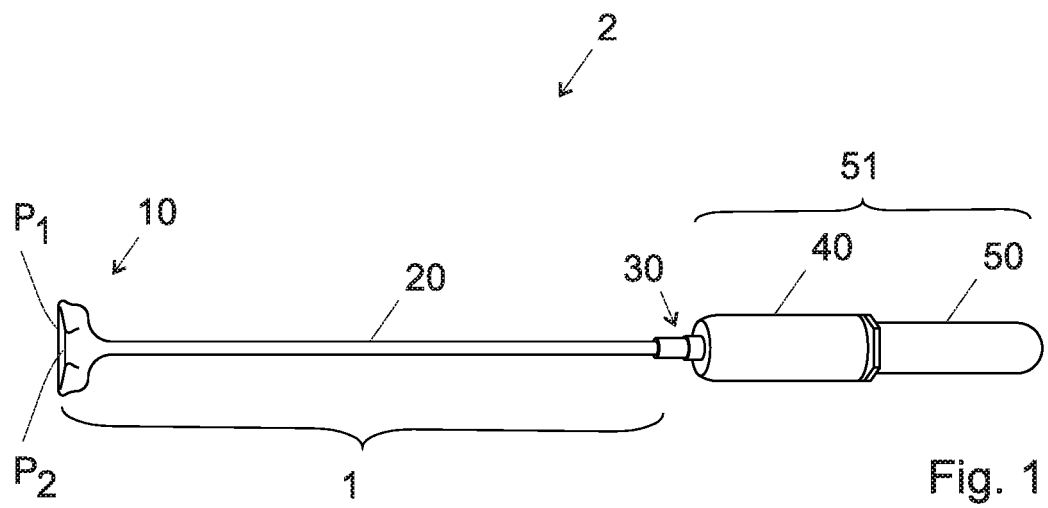
FIG. 1 shows a view of the whole apparatus in a first embodiment

FIG. 1 gives a general view of the whole apparatus 2 comprising, from the proximal end to the distal end, a vacuum system 51 including a vacuum reserve source 50 and a support of the vacuum reserve source 40, a connector 30 and the suction module 1. As known per se, the vacuum reserve source 50 and the support of the vacuum reserve source 40 cooperate to form a pump that can be manually activated by a reciprocal sliding motion of the vacuum reserve source 50 within the support 40 of the vacuum reserve source which has open proximal end (on the right side in FIG. 1) which can accommodate a segment of the vacuum tube. Alternatively, an electrical motor can activate the reciprocal motion.

The suction module 1 comprises a suction chamber 10 and a hollow rod 20.

Figure 2:
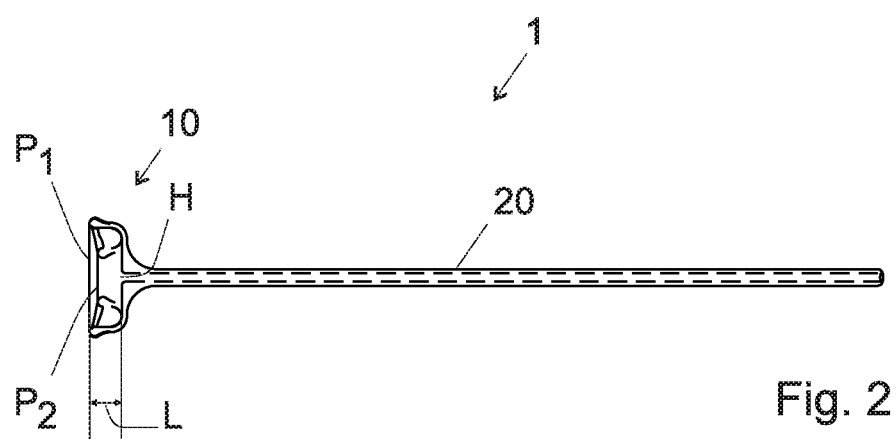
FIG. 2 shows a perspective view of the suction module with a straight hollow rod

In a variant the hollow rod 20 can be straight as illustrated in FIGS. 1 and 2.

Figure 3:
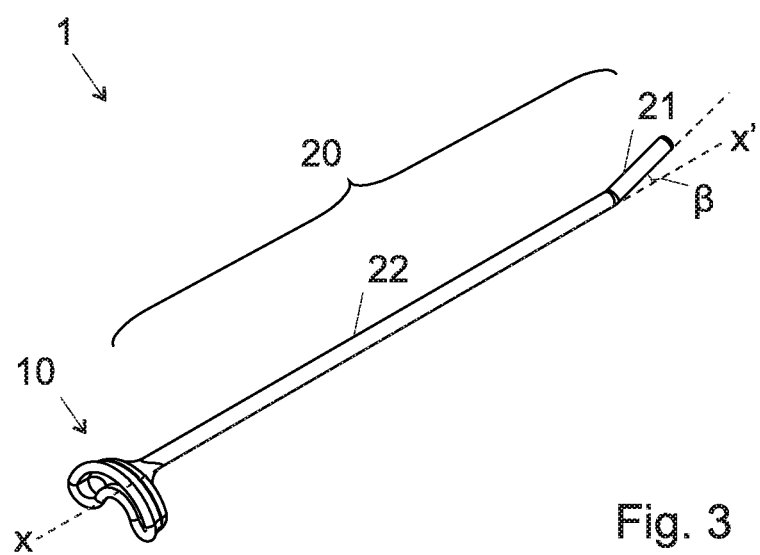
FIG. 3 shows a view of the suction module illustrating the curved portion of the hollow rod
Figure 6:
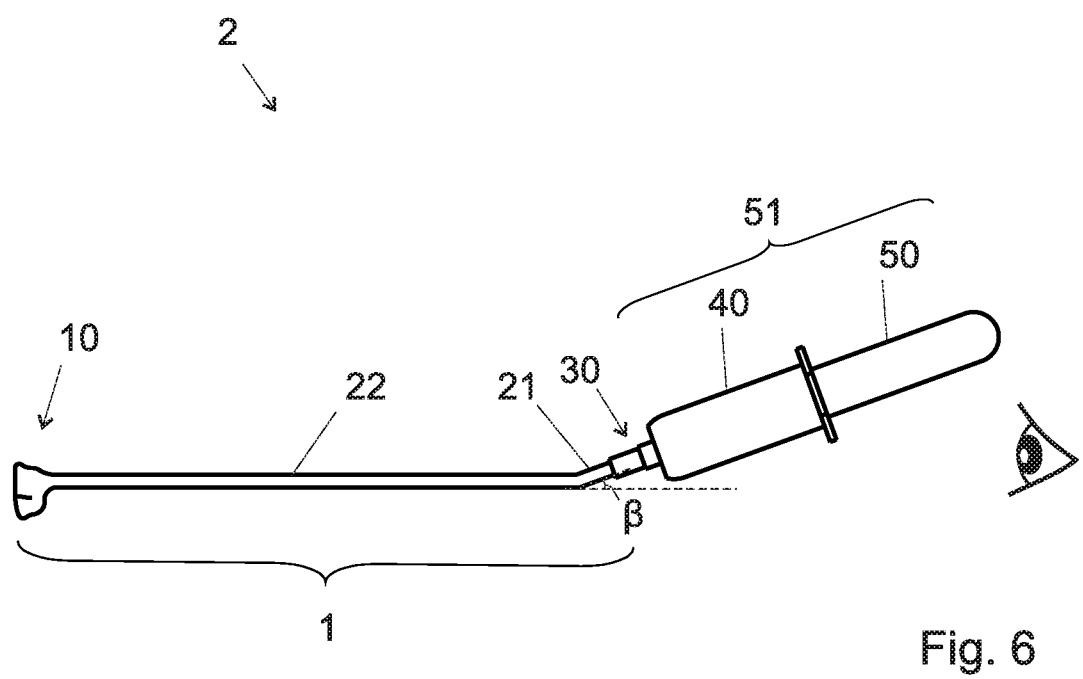
FIG. 6 shows a profile view of the whole apparatus illustrating the curved portion.
Figure 7:
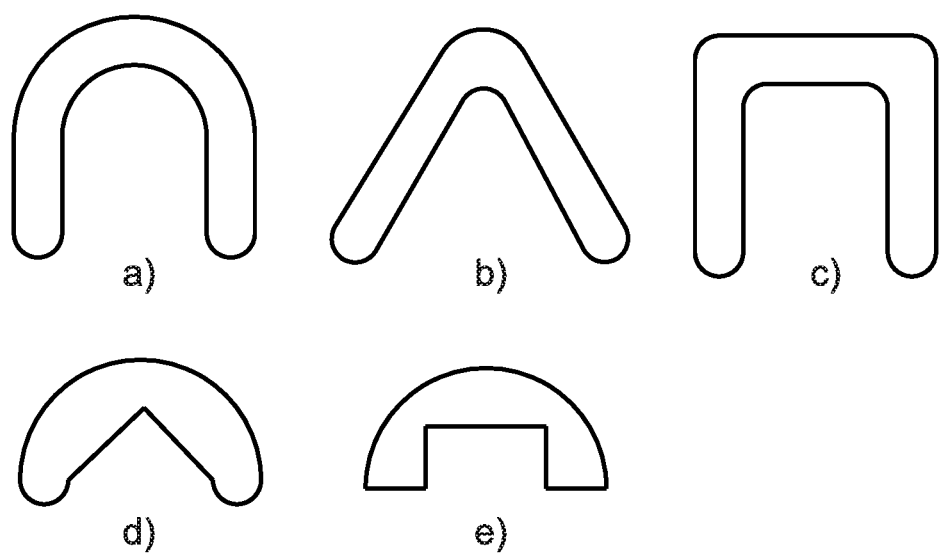
FIG. 7 shows different shapes of the suction module

In another variant the hollow rod 20 can include a straight part 22 and an inclined part 21 as illustrated in FIGS. 3 and 6.

Figure 4:
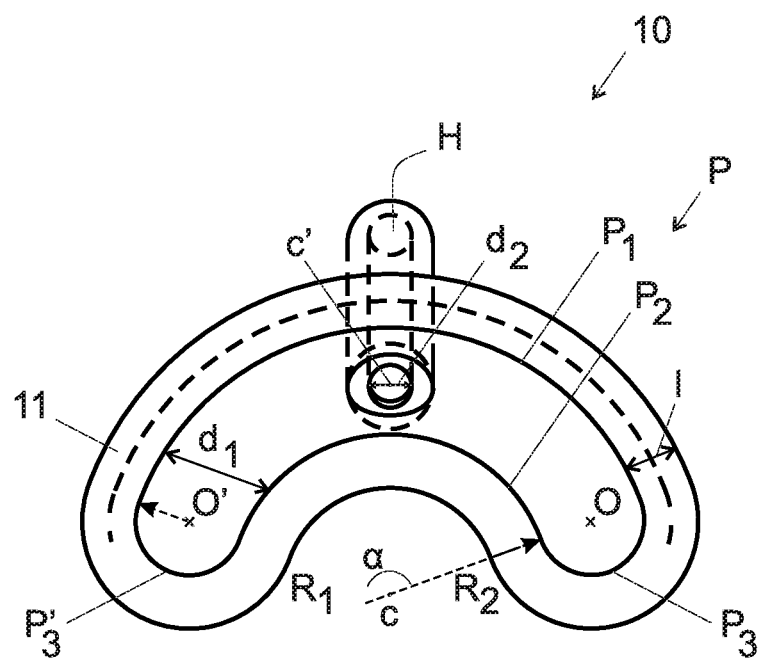
FIG. 4 shows a bottom view of the suction chamber
Figure 5:
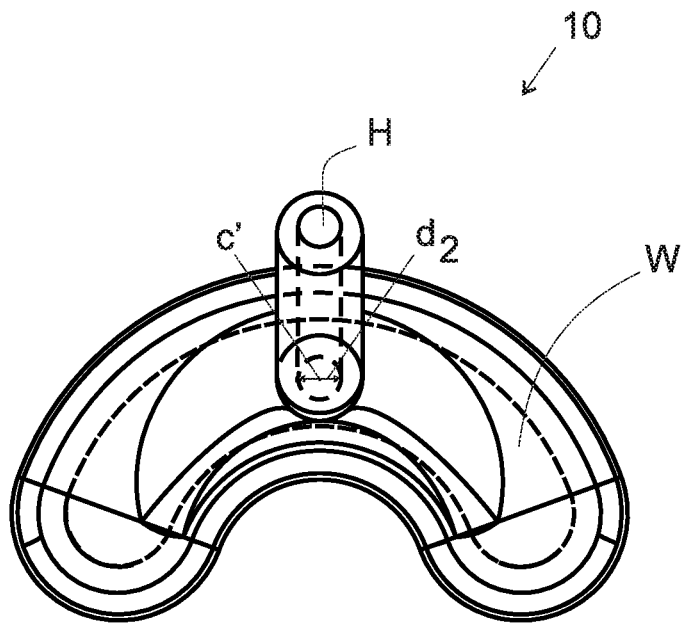
FIG. 5 shows a top view of the suction chamber

The suction chamber 10 also represented in FIGS. 4 and 5 is configured to engage the surface of the vaginal portion of a cervix like a suction pad. The suction chamber 10 has a general C or V or arc of a circle shape. The suction chamber 10 is delimited by a wall W which is concave in the direction opposite to the hollow rod 20 to define a space. This wall W is defined by an edge P which follows a line defining a closed loop having a C shape, i.e. a shape according to the outline of a capital U with arms of the U reduced to their minimum, namely almost reduced to the basis of the capital U, which corresponds to a capital C with rounded extremities. Also C shape means other similar shapes corresponding to a capital V with rounded extremities and basis or C-like shape or U-like shape or any of shape in FIGS. 7a, 7b, 7c, 7d and 7e represented in FIG. 7. In fact, the global shape of the suction chamber defines an open design, such as an arc of a circle, and not a closed design, such as a circle or an annulus. Therefore there is more room for the practitioner to place the surgical instrument between the arms of the C-shape defined by the suction chamber and make a mucus membrane swab sampling.

The wall edge comprises four portions having an arc of circle shape: an internal portion P2 of the edge, an external portion P1 of the edge, and two end portions P3 and P3' of the edge. The external edge portion P1 and the internal edge portion P2 are placed side by side with their curvature turned in the same direction. A first extremity of each of internal and external end portions P2 and P1 are connected together with the extremities of the end portions P3 (on the right of FIG. 4). A second extremity of each of internal and external end portions P2 and P1 are connected together with the other extremities of the end portion P3' (on the left of FIG. 4).

In one embodiment, as can be seen in FIG. 1 and FIG. 2, the internal edge P2 is out of the plane defined by the external portion P1. More precisely the internal edge P2 forms a depression in the proximal direction of the apparatus 2. In other words, the internal edge P2 is in rearward position with respect to the external portion P1 of the wall edge of the suction chamber 10. Such a gap, namely the difference in depth position between the internal edge P2 and the external portion P1 of the wall edge of the suction chamber 10, creates a contact surface for the suction chamber 10 which cannot be contained in a plane but which has a three-dimensional outline: such a geometry is adapted to the three-dimensional shape of the cervix. Preferably, the end portions P3 and P3' form a rounded zone between the external portion P1 and the internal portion P2.

In a variant not shown the internal edge P2, the external edge P1 and the end portion edges P3 and P3' are in the same plane.

Thanks to the C-shape defined by the edge P of the suction chamber 10, another instrument/device, not represented here, passing through the cervix, can be removed or inserted in the uterine cavity while the suction module 1 still engages a zone surface of a portion of the cervix surrounded by the edge P of the wall W. Easy insertion or removal of any instrument can be done in the uterine cavity while the suction module 1 grasps the cervix. Easy application or removal of the whole apparatus 2 can be done in the vaginal cavity while other instruments are inserted in the cervix. Stable grasping capability is enabled as this shape allows cervix dilatation while the suction module 1 grasps the cervix.

The C-shape encircles the external orifice of the cervix, distributes negative pressure in the suction chamber allowing unobstructed access to the external orifice of the cervix for insertion or removal of instruments or devices in/from the cervix as the suction module is engaged with the surface of the vaginal portion of the cervix and allowing dilatation of the cervix as the suction module is engaged with the surface of the vaginal portion of the cervix.

A through hole H is on the wall W and defines an orifice for the suction chamber 10. In one embodiment, the hole H is situated in the center C' of the wall W, as represented in FIG. 5, namely at equal distance between the external edge portion P1 and the internal edge portion P2 and also at equal distance between the end edge portion P3 and the end edge portion P3'. As represented in FIG. 2 the wall W measures a depth L (distance between the plane of the hole H and the external edge P1) between 3 and 20 mm or between 4 and 15 mm or between 5 and 10 mm preferably 8 mm.

The diameter d2 of the hole H is comprised between 0.1 and 20 mm or between 0.5 and 10 mm or between 1 and 5 mm preferably 3 mm.

The external edge portion P1, the internal edge portion P2 and the end portions P3 and P3' are curved and preferably arc of circles. The external edge portion P1 and the internal edge P2 define two angular sectors having the same center C, which is outside the outline of the edge P, and radii R1 and R2 respectively, with R2 smaller than R1. End portions P3 and P3' are semi arc of circle and have their respective centers O and O' placed inside the outline of the edge P and have radii which are equal to half d1, wherein d1 is the difference between the radii R1 and R2 of the two angular sectors.

The angular sectors of external portion P1 and the internal portion P2 extend over an angle α comprised between 10 and 350 degrees, preferably between 50 and 230 degrees, preferably between 100 and 180 degrees, preferably between 125 and 155. In a preferred embodiment the aforesaid angular sectors define an angle α of about 140 degrees for cervix's anatomies reasons.

For hygiene reasons and to prevent any risk of infection, the suction chamber 10 is disposable. Different tip size options given by the radii R1 and R2 of the external portion P1 and the internal portion P2, are available to best meet the anatomy of the cervix of each patient and ensure the efficiency of the instrument. The choice of the tip size option is made once the operator has visualized the cervix of the patient. The radii R1 and R2, are respectively 10 mm or 12.5 mm or 15 mm or 17.5 mm and 5 mm or 7.5 mm or 10 mm or 12.5 mm. The difference d1 given by R1-R2 which corresponds to the width of the suction chamber 10, is 5 mm. In other variants d1 is comprised between 1 mm and 50 mm, preferably between 2 mm and 25 mm, or between 3 mm and 10 mm.

To ensure a tightness between the suction module 1 and the cervix, a peripheral lip portion 11 is placed along the whole edge in radially outwardly direction of the external portion P1, of the internal portion P2 and of the ends portions P3 and P3' as illustrated in FIG. 4. This lip 11 has a width I between 1 and 10 mm or between 1 mm and 6 mm or between 2 mm and 4 mm, preferably 2.5 mm. Preferably, the lip has a semi-circular section with a radius between 0.5 mm and 5 mm or between 0.5 mm and 3 mm or between 1 mm and 2 mm.

To let a fluid establish pressure equilibrium within the apparatus 2 which is also sterilizable, the hollow rod 20 is used. In the FIGS. 1 to 6, the rod is made of one unique part with the suction chamber. However it can be assembled to the suction chamber 10 as separated element.

The hollow rod can be assembled to the vacuum system 51 using a mechanical attachment with or without O-rings, preferably a removable connection, therefore it is possible to separate the vacuum system with a hollow needle, not represented, which is placed between the hollow rod and the vacuum source 50, designed to pierce the closing rubber (not shown) of the vacuum reserve source 50 after using for special treatment.

The hollow rod 20, inserted in the vagina not represented, is a rigid tube to move/pull the suction chamber 10 accurately and precisely. It is made with material preferably transparent to offer a best in class visibility through the vagina and enhance the visibility for the practitioner. Of course medically approved materials are selected for the suction chamber and the rod 20, such as low and high density polyethylene or polypropylene or ethylene vinyl acetate or poly vinyl chloride or styrene ethylene butylene styrene or polyamide or polyether amide block copolymer or polyester or copolyester or polycarbonate or polyoxymethylene or poly ether etherketone or thermoplastic elastomer ether ester or polyethylene or butylene terephthalate Or polymethyl methacrylate or silicone or another human compatible polymer, or a medical grade glass, or a medical grade ceramic, or a medical grade metal such as stainless steel or titanium, or a combination of the previous cited materials.

The practitioner can then manipulate the cervix by mobilizing the rigid tube formed by the hollow rod 20, when the suction chamber 10 is in depression, i.e. at an air pressure lower than atmospheric pressure. The cervix traction reduces the kink between cervix and body of uterus for insertion of instruments into the uterine cavity.

As shown in FIGS. 3 and 6, the rigid hollow rod 20 has an inclined or curved portion 21 adjacent to an axial portion 22 of the rod to ensure an optimal field of view for the practitioner. The minimum angle β of the rod to an axis X-X' is defined by the volume and the size taken by a vacuum system 51 (vacuum reserve source 50 and support 40 of the vacuum reserve source with all its not represented subcomponents, forming guiding hand held element) to generate the best field of view for the practitioner while ensuring the largest range of manipulation. The angle β is comprised between 0 and 90 degrees, or between 5 and 70 degrees or between 10 and 50 degrees or between 15 and 30 degrees, preferably 20 degrees.

In a variant, the rod 20 can have a smooth curvature with a large radius.

This angle modification which is increasing the field of view for the practitioner, minimizes the risk of uterine perforation during insertion of instruments into the uterine cavity.

In this embodiment, the inclined or curved portion 21 of the hollow rod 20 measures between 1 and 50 mm or between 10 and 30 mm or between 15 and 25 mm preferably 20 mm.

The axial portion 22 of the hollow rod 20 measures a length between 10 and 300 mm or between 50 and 250 mm or between 80 and 200 mm or between 100 and 150 mm, preferably 130 mm.

In a variant, the vacuum system 51 is a single tuned level vacuum pump that may be in connection with a network of multiple devices throughout the clinic, the hospital or private office; the vacuum reserve source is a central vacuum source.

In another variant, the vacuum system 51 is a vacuum source with dual piston—while pressing on piston, piston pulls a second piston pulling the fluid and creates the vacuum (Alternating procedure syringe).

The vacuum system 51 comprises vacuum source such as a syringe VacLok™ type or Aspivenin™ type.

The whole apparatus 2 made for medical use is shown in FIG. 1 when the rod is straight and in FIG. 6 when the rod is inclined. This apparatus 2 comprises: the suction module 1, the vacuum system 51 a connector 30 to seal the rod with the vacuum reserve source.

The vacuum reserve source 50 has a pressure less than 500 mbar or less than 350 mbar or between 100 and 250 mbar, is depending on the global volume comprising the suction chamber and the rod.

In case the connector 30 is a part such as a cylindrical connection tube, a hollow needle, not represented is placed in the connector 30, designed to pierce the closing rubber (not shown) of the vacuum reserve source 50, allows vacuum release within the system; the pressure equilibrium within the system is then established, hence a suction force is applied on the cervix. In a variant the vacuum reserve source can be released one time only.

The connector 30, connecting the vacuum system 51 and the hollow rod 20 can be assembled by welding, gluing, or mechanical attachment with or without O-rings, preferably with a removable connection, therefore it is possible in certain case to separate the vacuum system with the needle after using for special treatment.

The suction chamber 10 when is engaged in a vaginal portion of a cervix, creates a crescent suction chamber against a surface of the vaginal portion of the cervix.

A vacuum system 51 generates partial vacuum between the suction chamber 10 and a patient's cervix. This enables the practitioners securing non-traumatically the upper end of the cervix to the suction module.

At the end of the medical procedure, the vacuum reserve source 50 is separated from the support 40 of the vacuum reserve source (for instance by being unscrewed) to balance the pressure and release the cervix. Eventually the suction module 1 is completely removed from the vagina by traction on the rigid rod 20 in the axis of the vagina.

FIGS. 8 to 11 now described are in relation to a second embodiment of the invention.

FIG. 8a gives a general view of the whole apparatus 2 comprising, from the distal end to the proximal end, the suction module 1 and a vacuum system comprising a vacuum reserve rod 60 defining a sealed enclosure and comprising an elongated portion with a distal end closed by a pierceable element 65.

Figure 9:
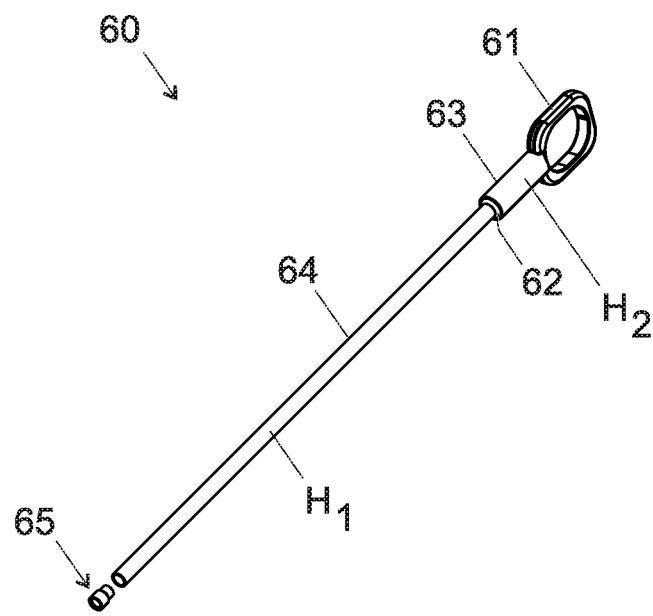
FIG. 9 shows an exploded view of the vacuum reserve rod according to said second embodiment FIGS. 10a and b show enlarged views of a portion of the suction module of FIG. 8

FIG. 9 shows an exploded view of the vacuum reserve rod 60. The elongated portion comprises three aligned portions extending along the main direction of the apparatus 2. The elongated portion has preferably two cylindrical first and second portions 63, 64 having different diameters, and a loop portion 61 attached to the first cylindrical portion 63. The distal end of the second portion 64 is closed by a pierceable element 65 making the vacuum reserve rod 60 defining a sealed enclosure and allowing maintaining the vacuum in the vacuum reserve rod 60.

The vacuum reserve rod 60 comprises a shoulder 62 along the elongated portion resulting from the diameter different between the two cylindrical parts 63 and 64. In the example shown in FIGS. 8a, 8b and 9 the outer face of the second cylindrical portion 64 has a diameter smaller than the diameter of the outer face of the first portion 63.

In a variant (not shown) other stop means can be used instead of the shoulder 62, such as a protruding flange ring, protruding tab(s) or lug(s) or any other mean placed along the elongated portion.

The second portion 64 has an outer diameter smaller than the diameter of the internal housing H' of the hollow rod 20 in order to be able to enter and slide within the hollow rod 20. The second portion 64 of the vacuum system rod 60 is directly housed into the passage H' of the hollow rod 20 shown in FIGS. 8*a*, 8*b* and 11. This second portion 64 is thus also intended to maintaining the vacuum reserve 60 partially inside the hollow rod 20, therefore in the suction module 1. Furthermore also in this example the first cylindrical portion 63 comprises a passage H2 which is preferably larger than the passage H1 of the second portion 64. This second passage H2 is not housed within the hollow rod 20 but stays outside the hollow rod 20. Therefore, this second passage H2 can be of bigger size in diameter than the passage H1 of the second portion 64 so that it allows more space for the sealed enclosure placed in under pressure (vacuum source).

The length of the second portion 64 is advantageously longer than the length of the first portion 63. The length of the second portion 64 can be longer than the length of the hollow rod 20. This ensures maintaining the vacuum reserve rod for a sufficient length in the suction module 1. As an example the cylindrical first portion 63 measures a length between 1 mm and 100 mm or between 10 mm and 60 mm or between 20 mm and 50 mm, preferably 35 mm. The cylindrical second portion 64 measures a length between 10 and 350 mm or between 100 and 300 mm or between 150 mm and 280 mm or between 180 mm and 260 mm, preferably 250 mm.

The loop portion 61 allows holding the vacuum rod 60 by the practitioner. The loop portion 61 can be hollow, allowing optimizing the volume available to create the vacuum in the vacuum reserve rod 60.

The hollow rod 20 and the suction chamber 10 are attached together by a connecting mean. The connecting mean is a connecting part 75 which delimits a cylindrical space A in which is inserted the end part B of the hollow rod 20, which is sealed by any suitable mean.

Figure 10A:
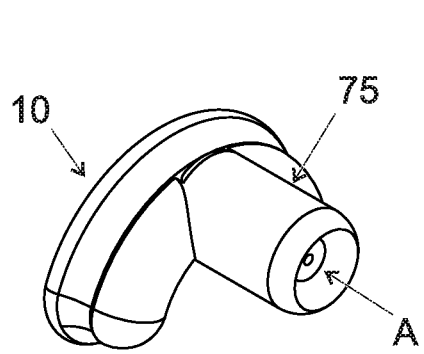
Figure 10B:
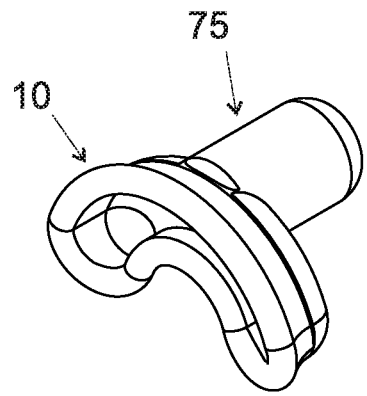

The connecting part 75 is one piece element with the suction chamber 10 as shown in FIGS. 10*a* and *b*. In a variant the connecting part 75 can be two pieces with the suction chamber 10 and sealed by any suitable mean.

As better shown in FIGS. 8*a* and *b*, a hollow needle 76 is mounted at the center of the cylindrical connecting part 75, which is able to connect in a sealed manner the suction chamber 10 to the hollow rod 20.

The needle 76 is configured to pierce the closing rubber 65 of the portion 64. This allows the vacuum releases within the system, therefore establishing the pressure equilibrium in the system.

In a variant the hollow needle 76 can be directly connected to the suction chamber 10. In this situation, according to one possible configuration the hollow needle 76 forms a one piece part with the suction chamber 10.

The hollow needle 76 can be placed within the suction chamber, in communication with the hole H, notably by overmolding both the cylindrical connecting part 75 and the suction chamber as a one piece part around the basement of the hollow needle, which tip protrudes.

In a variant the hollow needle 76 can be in two pieces with the suction chamber 10.

In another variant the hollow needle 76 can be positioned at various locations inside the hollow rod 20.

In another variant the assembler suction module 1, connecting part 75, hollow needle 76 and hollow rod 20 can be one piece. This one piece can be manufactured by using a printing 3D technology.

In another variant the assembler suction module 1, hollow needle 76 and hollow rod 20 can be one plastic piece. This one plastic piece can be manufactured by using a printing 3D technology (no connecting part 75 required).

FIG. 8*a* further shows the apparatus in a first position where the needle and the pierce element 65 are discarded. In this example the pierce element is not yet pierced, so the vacuum reserve rod 60 is intact.

When the practitioner needs to manipulate the cervix, he uses the apparatus 2 as follows. Initially, the apparatus 2 is in the first position as shown in FIG.8*a*. The practitioner holds a handle portion 80 fixed to the distal end of the hollow tube 20 by the holes of the handle 80 with the forefinger and the middle finger. Then he applies a force to the loop 61 using its thumb of the same hand, so that the second cylindrical portion 64 of the vacuum reserve rod 60 slides within the hollow rod 20 until it proximal end reaches the hollow needle 76 which pierces the closing rubber 65. Then, the apparatus 2 reaches a second position as shown in FIG. 8*b*, the last portion of displacement of the second cylindrical portion 64 within the hollow rod 20 leading to the abutment of the handle 80 against the shoulder 62 (not shown). The existing depression present in the vacuum reserve chamber 60 is transferred to the hole H when the pierceable element 65 is pierced by the hollow needle 76, which allows the adhesion of the suction chamber 10 to the cervix. The suction chamber 10 is in depression, i.e. at an air pressure lower than atmospheric pressure. The cervix traction reduces the kink between cervix and body of uterus for insertion of instruments into the uterine cavity.

The vacuum reserve source 60 has a pressure less than 350 mbar or less than 250 mbar or between 10 and 150 mbar, is depending on the global volume comprising the suction module 1, the two portions 63 and 64.

Figure 11:
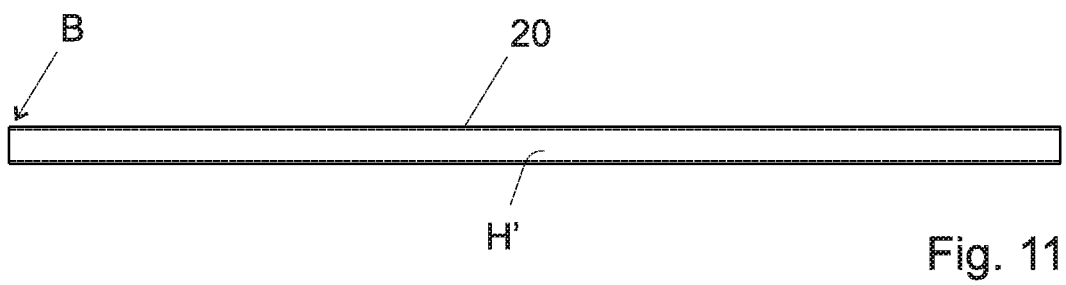
FIG. 11 shows a view of the hollow rod 20 of FIG. 8

The hollow rod 20 also shown in FIG. 11 and the vacuum reserve source 60 can be made with a rigid tube to move/pull the suction chamber 10 accurately and precisely. There are made with material preferably transparent to offer a best in class visibility through the vagina and enhance the visibility for the practitioner. Of course medically approved materials are selected such as low and high density polyethylene or polypropylene or ethylene vinyl acetate or poly vinyl chloride or styrene ethylene butylene styrene or polyamide or polyether amide block copolymer or polyester or copolyester or polycarbonate or polyoxymethylene or poly ether etherketone or thermoplastic elastomer ether ester or polyethylene or butylene terephthalate Or polymethyl methacrylate or silicone or another human compatible polymer, or a medical grade glass, or a medical grade ceramic, or a medical grade metal such as stainless steel or titanium, or a combination of the previous cited materials.

REFERENCE NUMBERS USED FOR THE FIGURES

1 Suction module
2 Whole apparatus
10 Suction chamber
20 Hollow rod
21 Inclined portion of the hollow rod
Axial portion of the hollow rod
β Angle between the inclined portion and an axis X-X'
W Wall
L Depth of the wall
P Edge
P1 External edge portion
P2 Internal edge portion
P3, P3' End portion edge portions
C Center of the angular sector
C' Center of the wall W
R1 Radius 1 of the angular sector
R2 Radius 2 of the angular sector
α Angle between the two radii 1 and 2 d1 Distance between P1 and P2
d2 Diameter of the hole
H hole
11 lip
I width of the lip
X-X' Longitudinal axis
O and O' Centers of P3 and P3'
30 Connector
40 Support of the vacuum reserve source
50 Vacuum reserve source
51 Vacuum system
60 Vacuum reserve rod
61 Loop portion
62 Shoulder
63 First cylindrical portion
64 Second cylindrical portion
65 Closing rubber
75 Cylindrical connecting part
76 Hollow needle
80 Handle portion
H' Passage in the hollow rod 20
H1 Passage in the portion 64
H2 Passage in the portion 63

The invention claimed is:

1. A gynecological suction module comprising:
   a hollow rod having a proximal end and a distal end; and
   a suction chamber connected to the distal end of the hollow rod by a hole for fluid connection, the suction chamber being configured to engage a surface of a vaginal portion of a cervix, the suction chamber being delimited by a wall having an edge,
   wherein the edge defines a C-shaped opening of the suction chamber such that the edge forms a closed loop surrounding the C-shaped opening, the edge comprising
   an external edge portion,
   an internal edge portion, and
   two end edge portions,
   wherein the internal edge portion is out of a plane defined by the external edge portion, such that the internal edge portion is disposed proximal of the external edge portion.

2. The gynecological suction module according to claim 1, wherein the closed loop of the edge is formed by the external edge portion, the internal edge portion and the two end edge portions, the two end edge portions connecting the external edge portion to the internal edge portion.

3. The gynecological suction module according to claim 2, wherein the external edge portion, the internal edge portion and the two end edge portions are curved, wherein curvatures of the external edge portion and of the two end edge portions are directed towards an inside of the closed loop of the edge and wherein a curvature of the internal edge portion is directed towards an outside of the closed loop of the edge.

4. The gynecological suction module according to claim 3, wherein the external edge portion, the internal edge portion and the two end edge portions are arcs of a circle.

5. The gynecological suction module according to claim 2, wherein the two end edge portions are semi-circles.

6. The gynecological suction module according to claim 2, wherein the external edge portion and the internal edge portion define respective angular sectors having a same center.

7. The gynecological suction module according to claim 1, wherein a peripheral lip portion is placed along the edge in a radially outwardly direction.

8. The gynecological suction module according to claim 7, wherein the peripheral lip portion has a semi-circular section with a radius between one of 0.5 and 5 mm, 0.5 and 3 mm, and 1 and 2 mm.

9. The gynecological suction module according to claim 1, wherein the hole is placed through the wall.

10. The gynecological suction module according to claim 1, wherein the hole is placed at an equal distance from the external edge portion and from the internal edge portion and also at equal distance between the two end edge portions.

11. The gynecological suction module according to claim 1, wherein the hollow rod is rigid to move/pull the gynecological suction module.

12. The gynecological suction module according to claim 1, wherein the hollow rod has an axial portion connected to the suction chamber and an inclined or curved portion adjacent to the axial portion to ensure an optimal field of view for a practitioner.

13. The gynecological suction module according to claim 12, wherein the inclined or curved portion of the hollow rod forms an angle with respect to a longitudinal axis of the axial portion which is comprised between one of 0 and 90 degrees, 5 and 70 degrees, 10 and 50 degrees, and 15 and 30 degrees.

14. The gynecological suction module according to claim 1, wherein the hollow rod is made with transparent material to enhance the visibility for a practitioner.

15. An apparatus for medical use comprising:
    the gynecological suction module according to claim 1; and
    a vacuum system.

16. The apparatus according to claim 15 comprising: a connector to seal the hollow rod with the vacuum system.

17. The apparatus according to claim 16, wherein the connector connecting the vacuum system and the hollow rod can be assembled by welding, gluing, or mechanical attachment with or without O-rings.

18. The apparatus according to claim 15, wherein the vacuum system is a vacuum reserve rod defining a sealed enclosure and comprising an elongated portion with a distal end closed by a pierceable element, the elongated portion being configured to be placed at least partially within the hollow rod of the gynecological suction module, the apparatus further comprising
    a hollow needle arranged for piercing the pierceable element of the vacuum reserve rod when the elongated portion of the vacuum reserve rod is placed at least partially within the hollow rod of the gynecological suction module whereby the suction chamber of the gynecological suction module is in tight fluid communication with the vacuum reserve rod.

19. The apparatus according to claim 18, wherein the elongated portion comprises a stop means.

20. The apparatus according to claim 18, wherein the elongated portion comprises first and second cylindrical portions that are attached together and wherein the vacuum reserve rod further comprises a loop portion at a proximal end.

21. The apparatus according to claim 20, wherein the second cylindrical portion has an outer diameter which is smaller than an inner diameter of the hollow rod.

22. The apparatus according to claim 20, wherein the first cylindrical portion comprises a first passage that is larger than a second passage of the second cylindrical portion.

23. The apparatus according to claim 18, wherein the pierceable element is one of a closing plastic layer, a rubber, a septum, and a plug.

24. The apparatus according to claim 18, wherein the hollow needle is mounted at the center of a cylindrical connecting part which is able to connect in a sealed manner the suction chamber to the hole of the hollow rod.

25. The apparatus according to claim 18, wherein the hollow needle is directly connected to the suction chamber.

* * * * *